United States Patent [19]

Kawato

[11] Patent Number: 6,139,854

[45] Date of Patent: Oct. 31, 2000

[54] SKIN LIGHTENING COMPOSITIONS

[75] Inventor: Junji Kawato, Omihachiman, Japan

[73] Assignee: The Procter & Gamble Company, Cincinnati, Ohio

[21] Appl. No.: 09/242,754

[22] PCT Filed: Aug. 21, 1996

[86] PCT No.: PCT/US96/13490

§ 371 Date: Feb. 22, 1999

§ 102(e) Date: Feb. 22, 1999

[87] PCT Pub. No.: WO98/07406

PCT Pub. Date: Feb. 26, 1998

[51] Int. Cl.[7] .............................. A61K 6/00; A61K 7/00; A61K 7/135
[52] U.S. Cl. .............................................. 424/401; 424/62
[58] Field of Search ....................... 424/401, 62

[56] References Cited

FOREIGN PATENT DOCUMENTS

| WO 95/23780 | 3/1995 | WIPO . |
| WO95/23780 | 5/1996 | WIPO .............................. A61K 7/48 |

OTHER PUBLICATIONS

Mahjour et al., "Effect of Egg Yolk Lecithins and Commercial Soybean Lecithins on *In Vitro* Skin Permeation of Drugs", Journal of Controlled Release, vol. 14, pp. 243–252 (1990).

*Primary Examiner*—Thurman K. Page
*Assistant Examiner*—S. Howard
*Attorney, Agent, or Firm*—Dara M. Kendall; Fumiko Tsuneki; Michael E. Hilton

[57] ABSTRACT

The present invention relates to a skin lightening composition comprising (a) a safe and effective amount of a compound of the formula (I)

[formula (I)]:

$$HO-\phantom{x}\bigcirc\phantom{x}-O-\bigcirc_{Z} \quad (I)$$

wherein Z is Oxygen or Sulfur,
(b) an average polarity solvent
(c) a polyhydric alcohol
(d) a solid fatty alcohol
(e) a nonionic surfactant
(f) water, and
(g) lecithin wherein at least a portion of the above components (a), (b), (c), (d), (e), (f) and (g) forms a liquid crystal.

19 Claims, No Drawings

SKIN LIGHTENING COMPOSITIONS

TECHNICAL FIELD

The present invention relates to the field of skin lightening. Specifically, the present invention relates to novel compositions comprising a liquid crystal which enhance skin penetration effect of specific hydroquinone derivatives for skin lightening.

BACKGROUND OF THE INVENTION

The specific hydroquinone as shown in formula (I) is known as a skin lightening compound. See WO9523780.

formula (I)

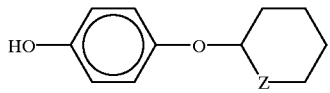

wherein Z is oxygen or sulfur.

The combination of the specific hydroquinone derivatives and penetration enhancers is disclosed in WO9523780.

WO9523780 describes that penetration enhancers are disclosed in Mahjour, M., B. Mauser, Z. Rashidbaigi & M. B. Fawzi, "Effect of Egg Yolk Lecithins and Commercial Soybean Lecithins on In Vitro Skin Permeation of Drugs", Journal of Controlled Release, Vol. 14 (1990), pp. 243–252. The journal discloses Lecithin as a penetration enhancer. However, there is no description of a liquid crystal comprising specific hydroquinone derivatives and lecithin which have penetration enhancing effect.

It is an object of the present invention to provide compositions for lightening mammalian skin which has a good penetration effect, so that the specific hydroquinone derivatives which are skin lightening actives can penetrate effectively and work effectively.

SUMMARY OF THE INVENTION

The present invention relates to a skin lightening composition comprising (a) a safe and effective amount of a compound of formula (I)

[formula (I)]:

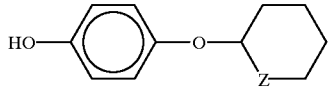

wherein Z is oxygen or sulfur.

(b) an average polarity solvent
(c) a polyhydric alcohol
(d) a solid fatty alcohol
(e) a nonionic surfactant
(f) water, and
(g) lecithin
wherein at least a portion of the above components (a), (b), (c), (d), (e), (f) and (g) forms a liquid crystal.

DETAILED DESCRIPTION OF THE INVENTION

The compound of the formula(I) have a good skin lightening effect in mammals, however it is expected to strengthen the penetration effect of the compound of formula (I) to mammal's skin. It has been unexpectedly found that the subject composition achieve good penetration in mammals' skin of the compounds of formula (I).

As used herein, "topical application" means directly laying on or spreading on outer skin.

As used herein, "skin lightening" means decreasing melanin in skin, including one or more of overall lightening of basal skin tone, lightening of hyperpigmented lesions including age spots, melasma, chloasma, freckles, post inflammatory hyperpigmentation or sun-induced pigmented blemishes.

As used herein, "solid" means solid form at the temperature of 25° C., and "liquid" means liquid form at the temperature of 25° C.

As used herein, all percentages are by weight unless otherwise specified.

The typical examples of the compound of fonnula(I) is as follows.

4-[(tetrahydro-2H-pyran-2-yl)oxy]phenol (hereinafter called THPOP).
4-[(tetrahydro-2H-thiopyan-2-yl)oxy]phenol.
These compounds are produced by the method described in WO9523780.

A skin lightening composition of the present invention comprises preferably from about 0.001% to about 10%, more preferably from about 0.01% to about 80/%, still more preferably from about 0.1% to about 5%, most preferably from about 0.5% to about 3% of the compound of the formula(I) as an active agent in a topical composition.

Use of subject compositions comprising over 3% of an active is preferred for lightening of hyperpigmented lesions and other areas where substantial lightening is desired.

Average Polarity Solvent

In order to dissolve the compounds of formula(I), since the compounds of formula(I) are molecules of average polarity being neither soluble in very polar solvents nor very non polar solvents, it is necessary to be dissolved in an average polarity solvent. The average polarity solvents could preferably be solvents which have the ratio of Organicity and Inorganicity (Organicity/Inorganicity) of 0.2 to 3.6, more preferably be solvents which have the ratio of Organicity and Inorganicity (Organicity/Inorganicity) of 0.5 to 3.5. The ratio of Organicity and Inorganicity (Organicity/Inorganicity) is described in Pharmaceutical Bulletin Vol. 2, No. 2, 163 (1954); and The Field of Chemical (Kagaku no Ryoiki) Vol. 11, No. 10, October 1957. The average polarity solvents include liquid triglycerides such as castor oil, olive oil, and capric/caprylic triglyceride; cosmetically acceptable ester oil such as isopropyl palmitate, oleyl oleate, 2-octyidodecyl myristate and neopentyl glycol dioctoanate (trade name: Cosmol 525 manufactured by Nisshin oil Mills LTD.); liquid fatty alcohols such as oleyl alcohol, isostearyl alcohol, lanolin alcohol, hexadecyl alcohol, octyidodecanol alcohol, linoleyl alcohol, linolenyl alcohol, arachidyl alcohol and 2-octyl dodecanol; liquid fatty acids such as oleic acid and isostearic acid; octyl methoxy cinnamate; cinoxate; and 2-ethylphexyl p-dimethyaninobenzoate. The following nonionic surfactants can be used as the average polarity solvents. Even if the following nonionic surfactants are used as the average polarity solvents, the other nonionic surfactants mentioned later (the "Nonionic surfactant" explanation part in this specification) are necessary for the present invention. Nonionic surfactants as the average polarity solvents include ethers of polyoxypropylene or polyoxyethylene and alphatic alcohol such as polyoxypropylene 15 stearyl ether and polyoxypropylene glycol 14 butyl ether;

polyoxypropylene or polyoxyethylene caster oils or hydrogenated caster oils such as polyoxyethylene (3) caster oil and polyoxyethylene (5) hydrogenated caster oil; polyoxypropylene or polyoxyethylene sorbitan fatty acid esters such as polyoxyethylene (20) sorbitan monooleate and sorbitan trioleate; polyoxypropylene or polyoxyethylene sorbit fatty acid esters such as polyoxyethylene (6) sorbitol tetraoleate; polyglycerin or glycerin fatty acid esters such as diglyceryl monooleate, glyceryl dioleate and glyceryl monoisostearate; polyoxypropylene or polyoxyethylene glycerin fatty acid esters such as polyoxyethylene (5) glyceryl monooleate; polyoxypropylene or polyoxyethylene alkyl phenyl ethers such as polyoxyethylene (2) nonylphenyl ether and polyoxyethylene (3) octylphenyl ether.

Among the average polarity solvents, either a liquid triglyceride or a cosmetically acceptable ester oil is preferred, and either capric/caprylic triglyceride or neopentyl glycol dioctoanate is more preferred. The good penetration effect is not obtained by the average polarity solvents per se but is obtained by said liquid crystal.

The amount of the average polarity solvents depend on the amount of the compounds of formula (I). However, the skin lightening composition of the present invention comprises preferably from 5% to 50% of the average polarity solvent, more preferably from 10% to 25% of the average polarity solvent.

Either one kind or two or more kinds of the average polarity solvent can be used in the present invention.

Polyhydric Alcohol

Polyhydric alcohols include glycerin, diglycerin, triglycerin, polyglycerin, polypropylene glycol, polyethylene glycol, ethylene glycol, diethylene glycol, triethylene glycol, propylene glycol, dipropylene glycol, hexylene glycol, 1,3-butylene glycol, 1,4-butylene glycol, ethylene glycol monoalkyl ether, diethylene glycol monoalkyl ether, glucose, maltose, sucrose, lactose, xylitose, xylitol, sorbitol, mannitol, maltitol, malbit, panthenol, pentaerythritol, and hyaluronic acid and its salts. Among the polyhydric alcohols, glycerin is preferred.

The skin lightening composition of the present invention comprises preferably from 0.1% to 10%, more preferably from 0.5% to 5% of the polyhydric alcohol.

Either one kind or two or more kinds of the polyhydric alcohol can be used in the present invention.

Solid Fatty Alcohol

Solid fatty alcohols include cetyl alcohol, stearyl alcohol, behenyl alcohol, myristyl alcohol, batyl alcohol, cholesterol and phytosterol. Among the solid fatty alcohols, cetyl alcohol is preferred.

The skin lightening composition of the present invention comprises preferably from 0.1% to 10%, more preferably from 0.5% to 3% of the fatty alcohol.

Either one kind or two or more kinds of the solid fatty alcohol can be used in the present invention.

Nonionic Surfactant

Nonionic surfactants include polyglycerin fatty acid esters, propylene glycol fatty acid esters, glycerin fatty acid esters, sorbitan fatty acid esters, sugar fatty acid esters, polyoxyethylene sorbitan fatty acid esters, polyoxyethylene sorbit fatty acid esters, polyethylene glycol fatty acid esters, polyoxyethylene glycerin fatty acid esters, polyoxyethylene castor oils, polyoxyethylene hardened castor oils, polyoxyethylene alkyl ethers, polyoxyethylene phytosterols, polyoxyethylene polyoxypropylene alkyl ethers, polyoxyethylene alkyl phenyl ethers, polyoxyethylene lanolins, polyoxyethylene lanolin alcohols, polyoxyethylene beeswax derivatives, polyoxyethylene fatty acid amides, polyether silicone derivatives, and polyoxyethylene fatty acid esters.

The nonionic surfactant could preferably be one which has HLB number of 10 to 17 and be solid at room temperature (25° C.). The preferable nonionic surfactants include polyoxyethylene(40) monostearate, polyoxyethylene(21) stearyl ether and decaglyceryl monostearate.

The skin lightening composition of the present invention comprises preferably from 0.1% to 5%, more preferably from 0.5% to 2% of the nonionic surfactant.

Either one kind or two or more kinds of the nonionic surfactant can be used in the present invention.

Water

The skin lightening composition of the present invention comprises preferably from 40% to 90%, more preferably from 60% to 80% of water.

Lecithin

Lecithin is a natural product derived from soybean or egg yolk.

The skin lightening composition of the present invention comprises preferably from 0.5% to 5%, more preferably from 2% to 3% of lecithin.

Combination Actives

A. Sunscreens and Sunblocks

Regulation of skin darkening resulting from exposure to ultraviolet light can be achieved by using combinations of the active skin lightening agents together with sunscreens or sunblocks. Useful sunblocks include, for example, zinc oxide and titanium dioxide.

Ultraviolet light is a predominant cause of skin darkening. Thus, for purposes of skin lightening, the combination of a skin lightening agent with a UVA and/or VB sunscreen is desirable, A wide variety of conventional sunscreening agents are suitable for use in combination with the skin lightening agent. Segarin, et al., at Chapter VIII pages 189 et seq., of *Cosmetics Science and Technology*, disclose numerous suitable agents. Specific suitable sunscreening agents include, for example: p-aminobenzoic acid, its salts and its derivatives (ethyl, isobutyl, glyceryl esters; p-methylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); Cinnarnic acid derivatives (menthyl and benzyl esters, butyl cinnamoyl pyruvate); dihydroxycinnamic acid derivatives (umbelliferone, methylumbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8disulfonic acids); dihydroxynaphthoic acid and its salts; o- and p-Hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol) (6-propyl piperonyl) ether, hydroquinone; benzophenones (oxybenzene, sulisobenzone, dioxybenzone, benzoresorcinol, 2,2',4,4'-tetrahydroxybenzophenone, 2,2'-dihydroxy4,4'-dimethoxybenzophenone, octabenzone; 4-isopropyldibenzoylmethane; butylmethoxydibenzoylmethane; etocrylene; and 4-isopropyl-di-benzoylmethane.

Of these, 2-ethylhexyl-p-methoxycinnamate, 4,4'-t-butyl methoxydibenzoyl-methane, 2-hydroxy-4- methoxybenzophenone, octyldimethyl-p-arninobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-axino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in the present invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methylaminobenzoic acid ester with 4-hydroxydibenzoylmethane; 4-N,N-(2-thylhexyl) methylaminobenzoic acid ester of 2-hydroxy-4-(2-hydroxy-ethoxy)benzophenone; 4-N,N-(2-ethylhexyl)-methylaminobenzoic acid ester of 4-(2-hydroxyethoxy) dibenzoylmethane N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

A safe and effective amount of sunscreen may be used in the compositions useful in the present invention. The sunscreening agent must be compatible with the skin lightening agent. The composition preferably comprises from about 1% to about 20%, more preferably from about 2% to about 10%, of a sunscreening agent. Exact amounts will vary depending upon the sunscreen chosen and the desired Sun Protection Factor (SPF).

An agent may also be added to any of the compositions useful in the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred skin lightening composition useful in the present invention, an anti-inflammatory agent is included as an active along with the skin lightening agent. The inclusion of an anti-inflammatory agent enhances the skin lightening benefits of the compositions. The anti-inflammatory agent protects strongly in the UVA radiation range (though it also provides some UVB protection as well). The topical use of anti-inflammtory agents reduces darkening of the skin resulting from chronic exposure to UV radiation. (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions useful in the present invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as bydrocortisone, hydroxyltriamcinolone, alpha-methyl dexamethasone, dexamethasone-phosphate, beclomethsone dipropionate, clobetasol valemate, desonide, desoxymethasone, desoxycorticosterone acetate, dexamethasone, dichlorisone, diflorasone diacetate, diflucortolone valerate, fluadrenolone, flu-clorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortmate, mepreddisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the non-steroidal anti-inflammatory agents. The variety of compounds encompassed by this group are well-known to those skilled in the art For detailed disclosure of the chemical structure, synthesis, side effects, etc., of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, aceinatacin, fentiazac, zomepiract, clidanac, oxepinac, and felbinac;

4) the fenamates, such as mefenarnic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenybutazone, oxyphenbutazone, feprazone, azapropazone, and trimethazone.

Mixtures of these non-steroidal anti-inflarnmatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the compositions are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di-tert-butyl phenol derivatives. For example, compounds selected from 4-(4'-pentyn-3'-one)-2,6-di-t-butylphenol; 4-(5'-hexynoyl)-2,6-di-t-butylphenol; 4-((S)-(–)-3'-methyl-5'-hexynoyl)-2,6-di-t-butylphenol; 4-((R)-(+)-3'-methyl-5'-hexynoyl)-2,6-di-t-butylphenol; and 4-3',3'-dimethoxypropionyl)-2,6-di-t-butylphenol are useful in methods of the present invention; 4-(5'-hexynoyl)-2,6-d-t-butylphenol is most preferred.

Yet another class of anti-inflammatory agents which are useful in the compositions are those disclosed in U.S. Pat. No. 4,912,248, Mueller, issued Mar. 27, 1990. This patent discloses compounds and diastereomeric mixtures of specific 2-naphtlilyl-containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen-(R)-2-butyl ester, and diasteromeric mixtures of (S)-naproxol-(R)-2-methyl butyrate and (S)-naproxol-(S)-2-methyl butyrate are useful in the present invention.

Finally, so-called "natural" anti-inflammatory agents are useful in methods of the present invention. For example, candelilla wax, alpha bisabolol, aloe vera, Manjistha (extracted from plants in the genus Rubia, particularly Rubia Cordifolia), and Guggal (extracted from plants in the genus Commiphora, particularly Commiphora Mukul), may be used.

Another preferred composition useful in the present invention comprises a skin lightening agent, a sunscreen, and an anti-inflammatory agent together for skin lightening in the amounts disclosed for each individually hereinabove.

C. Anti-Oxidants/Radical Scavengers

In a preferred skin lightening composition useful in the present invention, an anti-oxidant/radical scavenger is included as an active along with the skin lightening agent. The inclusion of an anti-oxidant/radical scavenger increases the skin lightening benefits of the composition.

A safe and effective amount of an anti-oxidant/radical scavenger may be added to the compositions useful in the present invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox☐), gallic acid and its alkyl esters, especially propyl gallate, uric acid and its salts and alkyl esters, sorbic acid and its salts, the ascorbyl esters of fatty acids, amines (e.g., N,N-diethylhydroxylamine, amino-guanidine), sulfhydryl compounds (e.g., glutathione), and dihydroxy fumaric acid and its salts may be used.

In a preferred composition useful in the present invention, compositions comprise one, any two, or all three of a sunscreening agent, anti-inflammatory agent, and/or an anti-oxidant/radical scavenging agent included as actives along with the skin lightening agent. The inclusion of two or all three of these agents with the skin lightening agent increases the skin lightening benefits of the composition.

D. Chelators

In a preferred composition useful in the present invention, a chelating agent is included as an active along with the skin lightening agent. As used herein, "chelating agent" means an active agent capable of removing a metal ion from a system by forming a complex so that the metal ion cannot readily participate in or catalyze chemical reactions. The inclusion of a chelating agent increases the skin lightening benefits of the composition.

A safe and effective amount of a chelating agent may be added to the compositions useful in the present invention, preferably from about 0.1% to about 10%, more preferably from about 1% to about 5%, of the composition. Chelators useful in compositions are disclosed in U.S. patent application Ser. No. 619,805, Bissett, Bush & Chatterjee, filed Nov. 27, 1990 (which is a continuation of U.S. patent application Ser. No. 251,910, filed Oct. 4, 1988), U.S. patent application Ser. No. 514,892, Bush & Bissett, filed Apr. 26, 1990; and U.S. patent application Ser. No. 657,847, Bush, Bissett & Chatterjee, filed Feb. 25, 1991; all incorporated herein by reference. Preferred chelators useful in compositions of the present invention are furildioxime and derivatives thereof In a preferred composition useful in the present invention, compositions comprise one, any two, any three, or all four of a sunscreening agent, anti-inflammatory agent, anti-oxidant/radical scavenging agent, and/or chelating agent included as actives along with the skin lightening agent. The inclusion of two, three, or all four of these agents with the skin lightening agent increases the skin lightening benefits of the composition.

E. Retinoids

In a preferred composition useful in the present invention, a retinoid, preferably retinoic acid, is included as an active along with the skin lightening agent. The inclusion of a retinoid increases the skin lightening benefits of the composition. A safe and effective amount of a retinoid may be added to the compositions useful in the present invention, preferably from about 0.001% to about 2%, more preferably from about 0.01% to about 1% of the composition. As used herein, "retinoid" includes all natural and/or synthetic analogs of Vitamin A or retinol-like compounds which possess the biological activity of Vitamin A in the skin as well as the geometric isomers and stereo isomers of these compounds, such as all-trans retinoic acid and 13-cis-retinoic acid.

In a preferred composition useful in the present invention, compositions comprise one, any two, any three, any four, and/or all five of a sunscreening agent, anti-inflammatory agent, anti-oxidantradical scavenging agent, chelating agent, and/or a retinoid included as actives along with the skin lightening agent. The inclusion of two, three, four, or all five of these agents with the skin lightening agent increases the skin lightening benefits of the composition.

Other Optional Components

Other optional components include thickeners such as carboxy vinyl polymer, preservatives, liquid and paste pigments, astringents, pH buffers, perfumes, infrared screening agents, amphoteric and solid amorphous lipids, vitamins, nutrients, and skin conditioning agents.

Useful skin conditioning agents are beta-glycyrrhetic acid and its derivatives, vegetation extracts, alantoin, collagen, and extract and treated elastin fibers.

The topical compositions useful in the present invention may be made into emulsion type product. These include, but are not limited to, milky lotions, creams and ointments.

The emulsion type product comprises a liquid crystal comprising the compound of formula (I), an average polarity solvent, a polyhydric alcohol, a fatty alcohol, a nonionic surfactant, water and lecithin.

Emulsions according to the present invention generally contain a cosmetically acceptable aqueous or organic solvent such as ethanol, isopropanol, sorbitol esters, and mixtures thereof and a lipid or oil. Lipids and oils may be derived from animals, plants, or petroleum and may be natural or synthetic (i.e., man-made).

The emulsion may also contain an anti-foaming agent to minimize foaming upon application to the skin. Anti-foaming agents include high molecular weight silicones and other materials well known in the art for such use.

The emulsions preferably comprise a silicone for imparting a preferred skin feel. Generally such silicones have a low molecular weight. Suitable such silicones include cyclomethicones, dimethicones, and blends such as Dow Corning 200 fluid (especially 10 cs) and Dow Corning Q2-1401. Such silicones are commercially available from the Dow Corning Corp. of Midland, Mich.

The skin lightening composition of the present invention may comprise a topical cosmetically acceptable emollient. As used herein, "emollient" refers to a material used for the prevention or relief of dryness, as well as for the protection of the skin. A wide variety of suitable emollients are known and may be used herein. Sagarin, Cosmetics, Science and Technology, 2nd Edition, Vol. 1, pp. 32–43 (1972), incorporated herein by reference, contains numerous examples of materials suitable as an emollient. The skin lightening cosmetic of the present invention typically comprises from about 5% to about 50%, preferably from about 10% to about 25%, of emollient.

Methods for Lightening Skin in Mammals

The present invention also relates to methods for skin lightening in mammals comprising topical application of the skin lightening composition of the present invention. The amount of active agent and frequency of application will vary widely depending upon the skin color already in existence in the subject, the rate of further darkening of the skin, and the level of lightening desired.

A safe and effective amount of skin lightening agent in a topical composition is applied, generally from about 1 g to about 10 g per $cm^2$ skin per application, preferably from about 2 g to about 8 g/$cm^2$ skin per application, more preferably from about 3 g to about 7 g/$cm^2$ skin, also preferably from about 4 g to about 5 g/$cm^2$ skin. Application preferably ranges from about four times a day to about twice a week, more preferably from about three times a day to about once every other day, more preferably still from about once daily to about twice daily. Application for at least five days is required to see a skin lightening effect in lower animals. Application for at least one month is required to see an effect in humans. After lightening is achieved, the frequency and dosage can be reduced to a maintenance level, as desired. Such maintenance varies according to the individual, but is preferably from about $1/10$ to about $1/2$, more preferably from about $1/5$ to about $1/3$ of the original dosage and/or frequency, as needed.

A preferred method of the present invention for skin lightening in mammals involves applying the skin lightening composition of the present invention further comprising a safe and effective amount of one or more of a sunscreening agent, an anti-inflammatory agent, an anti-oxidant/radical scavenging agent, a chelating agent and/or a retinoid. The amount of sunscreening agent applied is preferably from about 0.01 mg to about 0.1 mg per $cm^2$ skin. The amount of anti-inflammatory agent applied is preferably from about 0.005 mg to about 0.5 mg, more preferably from about 0.01 mg to about 0.1 mg per $cm^2$ skin. The amount of antioxidant/radical scavenging agent preferably applied is from about 0.01 mg to about 1.0 mg, more preferably from about 0.05 mg to about 0.5 mg per $cm^2$ skin. The amount of chelating agent preferably applied is from about 0.001 mg to about 1.0 mg, more preferably from about 0.01 mg to about 0.5 mg, still more preferably from about 0.05 mg to about 0.1 mg per $cm^2$ skin. The amount of retinoid applied is preferably from about 0.001 mg to about 0.5 mg per $cm^2$ skin, more preferably from about 0.005 mg to about 0.1 mg per $cm^2$ skin. The amount of skin lightening agent applied is preferably from about 0.001 mg to about 2 mg per $cm^2$ skin per application, more preferably from about 0.01 mg to about 1 mg per $cm^2$ skin per application.

Procedure for Making a Skin Lightening Composition of the Present Invention

For example, a skin lightening composition of the present invention which comprises a liquid crystal can be made by the steps of (i) mixing a safe and effective amount of a compound of the formula (I), an average polarity solvent, a fatty alcohol, a nonionic surfactant and lecithin at the temperature of 60° C. to 100° C. to obtain mixture 1, and (ii) mixing a polyhydric alcohol and water with the mixture 1 while maintained at the temperature of 45° C. to 100° C.

The mixture obtained by the above steps (i) and (ii) is usually cooled to room temperature.

The other component can be mixed according to the convention manner, however, generally oil-soluble components can be added in the above step (i) and water-soluble components can be added in the above step (ii).

The liquid crystal can be detected by observing the shape of the liquid crystal by a polarization microscope.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Test Example 1

Procedure for Making Control Composition

THPOP is dissolved in polypropylene glycol (14) butyl ether (THPOP phase-1) Separately, polyoxyethylene (21) stearyl alcohol, polyoxyethylene (2) stearyl alcohol, cetyl alcohol, stearyl alcohol, cyclomethicone and ascorbyl palmitate are dissolved at 70° C. and stirred well. The THPOP phase-1 is added thereto and mixed continuously. (THPOP phase-2)

In another vessel, all other ingredients than the above are dissolved at 70° C. (water phase)

The THPOP phase-2 and the water phase are mixed well and allowed to cool to obtain oil-in-water emulsion (o/w emulsion). The components of control is shown in Table 1.

Procedure for Making Test Composition No. 1

THPOP, caprylicicapric triglyceride (Migyol 812), cetyl alcohol, polyoxyethylene(40) monostearate and lecithin are mixed together and heated to 70° C. Then, deionized water and glycerin are added thereto with stirring and the mixture is emulsified. Then the emulsified mixture is cooled to room temperature with stirring to obtain an emulsion with a liquid crystal. The emulsion with the liquid crystal and all other ingredients than the above are mixed together to obtain Composition No. 1. The component of composition No. 1 is shown in Table 2.

Procedure for Making Test Composition No. 2

THPOP, neopentyl glycol dioctoanate (Cosmol 525), cetyl alcohol, polyoxyethylene(40) monostearate and lecithin are mixed together and heated to 70° C. Then, deionized water and glycerin are added thereto with stirring and the mixture is emulsified. Then the emulsified mixture is cooled to room temperature with stirring to obtain an emulsion with a liquid crystal. The emulsion with the liquid crystal and all other ingredients than the above are mixed together to obtain Composition No. 2. The component of composition No. 2 is shown in Table 3.

TABLE 1

Control (Oil in Water emulsion)

| Component | Amount (weight %) |
|---|---|
| De-ionized water | 75.70 |
| Hydrochloric Acid 1N | 2.30 |
| Triethanolamine | 1.40 |
| Mg Ascorbic Phosphate | 0.10 |
| Sodium Metabisulfite | 0.05 |
| Disodium EDTA | 0.05 |
| Polyoxyethylene (21) stearyl alcohol (21) | 2.00 |
| Polyoxyethylene (2) stearyl alcohol (2) | 1.00 |
| Polypropylene glycol (14) Butyl Ether | 7.50 |
| Cetyl Alcohol | 3.00 |
| Stearyl Alcohol | 1.50 |
| Cyclomethicone | 1.00 |
| Ascorbyl Palmitate | 0.10 |
| THPOP | 3.00 |
| Butylene glycol | 1.00 |
| Glydant Plus | 0.30 |

("Glydant Plus" is Dimethylol-5,5- dimethylhydantoin (and) Iodopropynyl Butyl carbamate)

TABLE 2

Composition No. 1

| Component | Amount (weight %) |
|---|---|
| Lecithin | 3.00 |
| Polyoxyethylene(40) monostearate (Myrj 52) | 1.00 |
| Cetyl Alcohol | 1.00 |
| Caprylic/Capric Triglyceride (Migyol 812) | 15.00 |
| D-delta Tocopherol | 0.10 |
| Glycerin | 5.00 |
| Propylparaben | 0.10 |
| Methylparaben | 0.20 |
| THPOP | 3.00 |
| De-ionized Water | 69.13 |
| Sodium Metabisulfite | 0.08 |
| Sodium Sulfite | 0.20 |
| Sodium Hydroxide | 0.59 |
| Carboxy vinyl polymer (Carbopol 980) | 1.00 |
| Benzyl Alcohol | 0.60 |

TABLE 3

Composition No. 2

| Component | Amount (weight %) |
|---|---|
| Lecithin | 3.00 |
| Polyoxyethylene(40) monostearate (Myrj 52) | 1.00 |
| Cetyl Alcohol | 1.00 |
| Neopentyl glycol dioctoanate (Cosmol 525) | 21.00 |
| D-delta Tocopherol | 0.10 |
| Glycerin | 5.00 |
| Propylparaben | 0.10 |
| Methylparaben | 0.20 |
| THPOP | 3.00 |
| De-ionized Water | 63.13 |
| Sodium Metabisulfite | 0.08 |
| Sodium Sulfite | 0.20 |
| Sodium Hydroxide | 0.59 |
| Carboxy vinyl polymer (Carbopol 980) | 1.00 |
| Benzyl Alcohol | 0.60 |

Test Method (1) Apparatus

The unjacketed diffusion cell is used. The cross-sectional area for penetration is 0.79 $cm^2$. This design is described by E. W. Merritt and E. R. Cooper, J. Controlled Release, 1(2), 161–162. Low glass tops that permit evaporation of the dose solution will be used for this study.

The diffusion cells are maintained at body temperature of 37° C. in aluminum blocks which sit in a stirring-heating module (Peirce Chemical Co.). Each aluminum block can accommodate six cells. The module controls the temperature and provides the stirring motor for the diffusion cells.

(2) Buffer Solution

The physiological saline solution used in this preparation is Dulbeco's phosphate buffered saline without calcium chloride and sodium bicarbonate (hereafter called "pbs") obtained from Wako Pure Chemical Industries LTD, CAM7276. Pbs is reconstituted with distilled water according to labeled instruction and 0.002% (s/v) sodium azide (Wako Pure Chemical Industries LTD, KCE 6293) is added to retard microbial growth. The pbs solution is maintained in a 37° C. water bath throughout the experiment in order to degas the solution. Evacuation of the solution using an aspirator, with stirring, for 15 minutes is also acceptable.

(3) Excised Human Cadaver Skin

Frozen excised human skin to a thickness of 0.25 mm (following washing and hair clipping) can be obtained from the Ohio Valley Skin and Tissue Center (Shriners Burns Institute, Cincinnati, Ohio). Skin is bathed in a solution of broad-spectrum antibiotics for 24 hours, treated with a 10% glycerol solution, wrapped in gauze, and placed in sealed sterile foil packs. The skin is cut into ~1.2×1.2 $cm^2$ using a scalpel (Keisei Medical industrial Co., handle #4, balde #21). The receptor compartments of the glass diffusion cells, filled with pbs solution (4–5 ml), are maintained at 37° C. in the aluminum blocks. The squares are mounted horizontally onto the cells with the stratum corneum facing the donor compartment and the dermis in contact with the receptor compartment. Non-occluded glass tops are placed onto the cells and firmly clamped in place. The aluminum blocks are placed back into the modules and micro magnetic stir bars are put into the receptor compartments of the cells to continually stir throughout the course of the experiment.

(4) Experimental Methods

The skin is allowed to equilibrate overnight, or for a minimum of 16 hours, with the dermis in contact with pbs solution and the stratum corneum exposed to air. A basic computer program is used to randomize the treatment groups and each diffusion cell is labeled accordingly. Following equilibration and just prior to dosing, the solution in the receptor compartment is discarded and refilled with fresh pbs solution. This procedure consists of pouring out the solution in the receptor compartment, rinsing with 2–3 ml of fresh pbs solution and refilling with fresh pbs solution. When pouring out solution, a gloved hand containing a magnet is used to prevent the micro stir bar from being expelled. Air bubbles which collect on the dermal surface of the skin are removed by holding the glass cell at an angle and gently tapping. Temperature of the solution in the receptor compartment is randomly observed, and adjusted if necessary, throughout the course of the experiment using a SATO PAC-9400 thermocouple thermometer.

(5) Dosing and Sampling Procedures

Test compositions and controls are dosed onto the stratum corneum (donor compartment) using a pipettor. If a small volume of material is dosed, the pipette tip is used to distribute the material evenly over the skin. If occlusion is called for, a small piece of parafilm is placed over the glass top immediately following dosing. Receptor compartment samples are usually collected 6 and 24 hours post-dose. Sampling consists of pouring the solution from the receptor compartment into a vial, risining with 2–3 ml of pbs solution and adding this rinse to the vial, then refilling with fresh pbs solution. Blank samples (pbs solution only) are obtained after each collection period and used for the background determination. Dummy dosing solution aliquots are weighed into scintillation vials for HPLC analysis in order to calculate the average dose applied to each cell. Aliquots from a prepared solution of test material and ethanol are also submitted for HPLC analysis to standardize the results and establish a conversion factor for the data analysis.

(6) Cleaning Procedures

At the end of the experiment, cells are dismantled and washed in a strong detergent solution (Alconox), rinsed with distilled water and allowed to air dry. Skin is wrapped in foil and stored in the freezer prior to disposal by incineration. In case of lacking incineration facility, a concentrated $H_2SO_4$ bath can be used to dissolve skin. Stir bars are rinsed and placed overnight in a beaker containing ethanol. Clamps are rinsed in distilled water and occasionally washed in an Alconox solution.

(7) HPLC Analysis

The penetration samples and aliquots of dosing and standard solutions are then analyzed for THPOP% by HPLC, (High Performance Liquid Chromatography-Shimazu LC-9A using JSPHERE ODS M80 Column)

Penetration value was calculated by the following equation.

Penetration value(%)=penetrated amount of THPOP at each time point(mg)×100 amount of THPOP in applied composition(mg)

The test result is shown in Table 4.

TABLE 4

| Tested composition | Penetration value (%) in each time | |
|---|---|---|
| | 6 hrs | 24 hrs |
| Composition No. 1 | 5.20 | 18.07 |
| Composition No. 2 | 6.47 | 23.92 |
| Control | 2.94 | 6.54 |

As shown in the above Table 4, excellent penetration enhancing effect can be obtained by the composition No. 1 and the composition No. 2 of the present invention.

What is claimed is:

1. A skin lightening composition comprising
   (a) a safe and effective amount of a compound of the formula (I)

[formula (I)]:

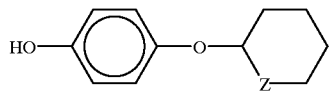

wherein Z is Oxygen or Sulfur,
   (b) an average polarity solvent
   (c) a polyhydric alcohol
   (d) a solid fatty alcohol
   (e) a nonionic surfactant
   (f) water, and
   (g) lecithin
   wherein at least a portion of the above components (a), (b), (c), (d), (e), (f) and (g) forms a liquid crystal.

2. A skin lightening composition comprising by weight to the entire composition
   (a) 0.001–10% of a compound of the formula (I)

[formula (I)]:

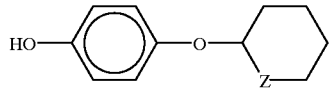

wherein Z is Oxygen or Sulfur,
   (b) 5–50% of an average polarity solvent
   (c) 0.1–10% of a polyhydric alcohol
   (d) 0.1–10% of a solid fatty alcohol
   (e) 0.1–5% of a nonionic surfactant
   (f) 40–90% of water, and
   (g) 0.5–5% of lecithin
   wherein at least a portion of the above components (a), (b), (c), (d), (e), (f) and (g) forms a liquid crystal.

3. The composition of claim 2 wherein Z is Oxygen.

4. The composition of claim 2 wherein Z is Sulfur.

5. The composition of claim 2 wherein the compound of the formula (I) is dissolved in the average polarity solvent.

6. The composition of claim 2 wherein the average polarity solvent has the ratio of Organicity and Inorganicity of 0.2 to 3.6.

7. The composition of claim 2 wherein the average polarity solvent is a liquid triglyceride.

8. The composition of claim 2 wherein the average polarity solvent is a cosmetically acceptable ester oil.

9. The composition of claim 2 wherein the average polarity solvent is capric/caprylic triglyceride.

10. The composition of claim 2 wherein the average polarity solvent is neopentyl glycol dioctoanate.

11. The composition of claim 2 wherein the polyhydric alcohol is glycerin.

12. The composition of claim 2 wherein the solid fatty alcohol is cetyl alcohol.

13. The composition of claim 2 wherein the nonionic surfactant has HLB of 2 to 20.

14. The composition of claim 2 wherein the nonionic surfactant is polyoxyethylene(40) monosteamate.

15. The composition of claim 2 wherein the composition is a topical composition.

16. An emulsion composition which comprises said liquid crystal according to claim 2.

17. A cream composition which comprises said liquid crystal according to claim 2.

18. A method for skin lightening in mammals which comprises topical application of skin lightening composition according to claim 1.

19. A process for preparing a skin lightening composition comprising a liquid crystal which comprises the steps of
(i) mixing by weight to the entire composition
(a) 0.001–10% of a compound of the formula (I)

[formula (I)]:

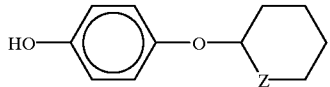

wherein Z is Oxygen or Sulfur,
(b) 5–50% of an average polarity solvent
(c) 0.1–10% of a solid fatty alcohol
(d) 0.1–5% of a nonionic surfactant, and
(e) 0.5–5% of lecithin at the temperature of 60° C. to 100° C. to obtain mixture 1, and (ii) mixing with the mixture 1 by weight to the entire composition
(f) 0.1–10% of a polyhydric alcohol, and
(g) 40–90% of water while maintained at the temperature of 45° C. to 100° C.

* * * * *